(12) United States Patent
Dwork et al.

(10) Patent No.: US 7,769,707 B2
(45) Date of Patent: Aug. 3, 2010

(54) DATA DIAMETER PRIVACY POLICIES

(75) Inventors: Cynthia Dwork, San Francisco, CA (US); Frank D. McSherry, San Francisco, CA (US)

(73) Assignee: Microsoft Corporation, Redmond, WA (US)

( * ) Notice: Subject to any disclaimer, the term of this patent is extended or adjusted under 35 U.S.C. 154(b) by 198 days.

(21) Appl. No.: 11/291,131

(22) Filed: Nov. 30, 2005

(65) Prior Publication Data

US 2007/0124268 A1 May 31, 2007

(51) Int. Cl.
*G06F 17/30* (2006.01)
(52) U.S. Cl. .............................................. 707/3; 707/9
(58) Field of Classification Search ........................ None
See application file for complete search history.

(56) References Cited

U.S. PATENT DOCUMENTS

| | | |
|---|---|---|
| 4,141,071 A | 2/1979 | Yerkes et al. |
| 5,794,178 A | 8/1998 | Caid et al. |
| 6,253,203 B1 | 6/2001 | O'Flaherty et al. |
| 6,345,252 B1 | 2/2002 | Beigi et al. |
| 6,636,887 B1 | 10/2003 | Augeri |
| 7,043,640 B2 | 5/2006 | Pritchard et al. |
| 7,162,456 B2 | 1/2007 | de Jong |
| 7,363,192 B2 | 4/2008 | Dwork et al. |
| 2001/0042068 A1 | 11/2001 | Yoshida et al. |
| 2002/0010679 A1 | 1/2002 | Felsher |
| 2002/0065884 A1 | 5/2002 | Donoho et al. |
| 2002/0157020 A1 | 10/2002 | Royer |
| 2003/0126139 A1 | 7/2003 | Lee et al. |
| 2003/0204498 A1 | 10/2003 | Lehnert |
| 2003/0229598 A1 | 12/2003 | de Jong |
| 2004/0103066 A1 | 5/2004 | Staddon et al. |
| 2004/0133927 A1 | 7/2004 | Sternberg et al. |
| 2004/0153456 A1 | 8/2004 | Charnock et al. |
| 2005/0021488 A1 | 1/2005 | Agrawal et al. |
| 2005/0183072 A1 | 8/2005 | Horning et al. |
| 2005/0246391 A1 | 11/2005 | Gross |
| 2005/0283455 A1 | 12/2005 | Kemmer et al. |
| 2006/0200431 A1 | 9/2006 | Dwork et al. |
| 2006/0259263 A1 | 11/2006 | Ashley et al. |
| 2007/0022125 A1 | 1/2007 | Salam et al. |
| 2007/0054646 A1 | 3/2007 | Smith |
| 2007/0083493 A1 | 4/2007 | Dwork et al. |
| 2007/0124268 A1 | 5/2007 | Dwork et al. |

(Continued)

OTHER PUBLICATIONS

Ben-Or, M., et al., "Completeness theorems for non-cryptographic fault-tolerant distributed computation," *ACM*, 1988, 1-10.

(Continued)

*Primary Examiner*—Hosain T Alam
*Assistant Examiner*—Ann J Chempakaseril
(74) *Attorney, Agent, or Firm*—Woodcock Washburn LLP (57) ABSTRACT

Privacy of data can be preserved while utility of the output is maximized by selecting from an appropriately calculated distribution of noise values to add to an output. A distribution that includes a high likelihood of large noise values may lead to less useful output data. Conversely, a distribution that includes very low likelihood of large noise values may lead to less privacy. A distribution should be calculated to provide an appropriate level of output utility and privacy based on the query that is performed and the desired privacy level.

13 Claims, 4 Drawing Sheets

U.S. PATENT DOCUMENTS

| | | | |
|---|---|---|---|
| 2007/0130147 | A1 | 6/2007 | Dwork et al. |
| 2007/0136027 | A1 | 6/2007 | Dwork et al. |
| 2007/0143289 | A1 | 6/2007 | Dwork et al. |
| 2007/0147606 | A1 | 6/2007 | Dwork et al. |
| 2007/0150437 | A1 | 6/2007 | Dwork et al. |
| 2009/0254971 | A1 | 10/2009 | Herz et al. |

OTHER PUBLICATIONS

Blum, A., et al., "Practical privacy: . . . The SuLQ framework," *PODS*, 2005, 128-138.

Chawla, S., et al., "On the utility of privacy-preserving histograms," *UAI*, 2005, 120-127.

Chawla, S., et al., "Toward privacy in public databases," *Theory of Cryptography Conference*, 2005, 363-385.

Dwork, et al., "Privacy-preserving datamining in vertically partitioned databases," *Crypto*, 2004, 17 pages.

Goldreich, O., et al., "How to play any mental game," *ACM*, 1987, 218-229.

Killian, J., "Secure Computation," *Cryptography Tutorial*, http://www.cs.rutgers.edu/~jkilian/lectures, downloaded from the Internet on Feb. 27, 2006.

U.S. Appl. No. 11/244,800, filed Oct. 6, 2005, Dwork, et al.

U.S. Appl. No. 11/292,884, filed Dec. 2, 2005, Dwork, et al.

U.S. Appl. No. 11/298,563, filed Dec. 9, 2005, Dwork, et al.

U.S. Appl. No. 11/305,800, filed Dec. 16, 2005, Dwork, et al.

U.S. Appl. No. 11/316,761, filed Dec. 22, 2005, Dwork, et al.

United States Patent and Trademark Office: Non-Final Office Action dated Mar. 11, 2008, U.S. Appl. No. 11/316,761, 14 pages.

United States Patent and Trademark Office: Non-Final Office Action dated Jan. 9, 2008, U.S. Appl. No. 11/305,800, 16 pages.

United States Patent and Trademark Office: Non-Final Office Action dated Nov. 9, 2007, U.S. Appl. No. 11/244,800, 18 pages.

Online Encyclopedia Entry, "Side-Channel Attack," Wikipedia, published Oct. 13, 2008, pp. 1-4.

Unknown, "Side Channel Attack," Wikipedia, published Jul. 18, 2004, pp. 1-3.

Dwork et al., "Privacy-Preserving Datamining on Vertically Partitioned Databases," Microsoft Research, published Jun. 30, 2004, pp. 1-17.

Evfimievski, Alexandre Valentinovich; Privacy Preserving Information Sharing, A Dissertation Presented to the Faculty of the Graduate School of Cornell University I Partial Fulfillment of the Requirements for the Degree of Doctor of Philosophy, Aug. 2004.

Hore, Bijit et al.; A Privacy-Preserving Index for Range Queries, Proceedings of the 30th VLDB Conference, Toronto, Canada, 2004.

In the United States Patent and Trademark Office, Non Final Rejection dated Jun. 6, 2008, 17 pages, in U.S. Appl. No. 11/292,884, filed Dec. 2, 2005.

In the United States Patent and Trademark Office, Final Rejection dated Jan. 6, 2009, 15 pages, in U.S. Appl. No. 11/292,884, filed Dec. 2, 2005.

In the United States Patent and Trademark Office, Notice of Allowance dated Apr. 16, 2009, 4 pages, in U.S. Appl. No. 11/292,884, filed Dec. 2, 2005.

In the United States Patent and Trademark Office, Notice of Allowance dated Aug. 20, 2009, 9 pages, in U.S. Appl. No. 11/316,791, filed Dec. 22, 2005.

In the United States Patent and Trademark Office, Non Final Rejection dated Feb. 9, 2007, 8 pages, in U.S. Appl. No. 11/298,563, filed Dec. 9, 2005.

In the United States Patent and Trademark Office, Final Rejection dated Aug. 13, 2007, 7 pages, in U.S. Appl. No. 11/298,563, filed Dec. 9, 2005.

In the United States Patent and Trademark Office, Advisory Action dated Oct. 24, 2007, 3 pages, in U.S. Appl. No. 11/298,563, filed Dec. 9, 2005.

In the United States Patent and Trademark Office, Notice of Allowance dated Jan. 10, 2008, 3 pages, in U.S. Appl. No. 11/298,563, filed Dec. 9, 2005.

In the United States Patent and Trademark Office, Non Final Rejection dated Mar. 11, 2008, 8 pages, in U.S. Appl. No. 11/316,761, filed Dec. 22, 2005.

In the United States Patent and Trademark Office, Final Rejection dated Oct. 15, 2008, 13 pages, in U.S. Appl. No. 11/316,761, filed Dec. 22, 2005.

In the United States Patent and Trademark Office, Non Final Rejection dated Mar. 18, 2009, 12 pages, in U.S. Appl. No. 11/316,761, filed Dec. 22, 2005.

In the United States Patent and Trademark Office, Non Final Rejection dated May 21, 2008, 16 pages, in U.S. Appl. No. 11/305,800, filed Dec. 16, 2005.

In the United States Patent and Trademark Office, Final Rejection dated Sep. 29, 2008, 15 pages, in U.S. Appl. No. 11/305,800, filed Dec. 16, 2005.

In the United States Patent and Trademark Office, Advisory Action dated Jan. 7, 2009, 3 pages, in U.S. Appl. No. 11/305,800, filed Dec. 16, 2005.

In the United States Patent and Trademark Office, Non Final Rejection dated Apr. 29, 2009, 10 pages, in U.S. Appl. No. 11/305,800, filed Dec. 16, 2005.

In the United States Patent and Trademark Office, Final Rejection dated May 30, 2008, 13 pages, in U.S. Appl. No. 11/244,800, filed Oct. 6, 2005.

In the United States Patent and Trademark Office, Advisory Action dated Sep. 18, 2008, 3 pages, in U.S. Appl. No. 11/244,800, filed Oct. 6, 2005.

In the United States Patent and Trademark Office, Non Final Rejection dated Jan. 23, 2009, 15 pages, in U.S. Appl. No. 11/244,800, filed Oct. 6, 2005.

In the United States Patent and Trademark Office, Final Rejection dated Jul. 20, 2009, 16 pages, in U.S. Appl. No. 11/244,800, filed Oct. 6, 2005.

In the United States Patent and Trademark Office, Non Final Rejection dated Nov. 19, 2007, 12 pages, in U.S. Appl. No. 11/244,800, filed Oct. 6, 2005.

In the United States Patent and Trademark Office, Final Rejection dated Oct. 23, 2009, 14 pages, in U.S. Appl. No. 11/316,761, filed Dec. 22, 2005.

In the United States Patent and Trademark Office, Non-Final Rejection dated Jan. 6, 2010, 22 pages, in U.S. Appl. No. 11/244,800, filed Oct. 6, 2005.

In the United States Patent and Trademark Office, Notice of Allowance dated Oct. 30, 2009, 8 pages, in U.S. Appl. No. 11/305,800, filed Dec. 16, 2005.

FIG. 1

Exponential Distribution
FIG. 2A

Normal Distribution
FIG. 2B

Hybrid Distribution
FIG. 2C

DATA DIAMETER PRIVACY POLICIES

BACKGROUND

Data collection is used to gather information for a wide variety of academic, business, and government purposes. For example, data collection is necessary for sociological studies, market research, and in the census. To maximize the utility of collected data, all data can be amassed and made available for analysis without any privacy controls. Of course, most people and organizations ("privacy principals") are unwilling to disclose all data, especially in modern times when data is easily exchanged and could fall into the wrong hands. Privacy guarantees can improve the willingness of privacy principals to contribute their data, as well as reduce fraud, identity theft, extortion, and other problems that can arise from sharing data without adequate privacy protection.

A method for preserving privacy is to compute collective results of queries performed over collected data, and disclose such collective results without disclosing the inputs of the participating privacy principals. For example, a medical database might be queried to determine how many people in the database are HIV positive. The total number of people that are HIV positive can be disclosed without disclosing the names of the individuals that are HIV positive. Useful data is thus extracted while ostensibly preserving the privacy of the principals to some extent.

However, as one might imagine, clever adversaries might apply a variety of techniques to predict or narrow down the set of individuals from the medical database who are likely to be HIV positive. For example, an adversary might run another query that asks how many people both have HIV and are not named John Smith. The adversary may then subtract the second query output from the first, and thereby learn the HIV status of John Smith without ever directly asking the database for a name of a privacy principal. With sensitive data, it is useful to provide verifiable privacy guarantees. For example, it would be useful to verifiably guarantee that nothing more can be gleaned about any specific privacy principal than was known at the outset.

Adding noise to a query output can enhance the privacy of the principals. Using the example above, some random number might be added to the disclosed number of HIV positive principals. The noise will decrease the accuracy of the disclosed output, but the corresponding gain in privacy may warrant this loss. The concept of adding noise to a query result to preserve the privacy of the principals is discussed in U.S. patent application Ser. No. 11/244,800; U.S. patent application Ser. No. 11/305,800, U.S. patent application Ser. No. 11/292,884, U.S. patent application Ser. No. 11/316,791, U.S. patent application Ser. No. 11/298,563,and U.S. patent application Ser. No. 11/316,761. Some additional work on privacy includes Chawla, Dwork, McSherry, Smith, and Wee, "Toward Privacy in Public Databases," Theory of Cryptography Conference, 2005; Dwork, Nissim, "Privacy-Preserving Data Mining in Vertically Partitioned Databases," Crypto 2004; Blum, Dwork, McSheffy, Nissim, "Practical Privacy: The SuLQ Framework," PODS 2005; and Chawla, Dwork, McSheffy, Talwar, "On the Utility of Privacy-Preserving Histograms," UAI 2005.

Even when noise is added to results, adversaries may be able to glean information about privacy principals by running a multitude of queries and comparing the outputs. This problem can be addressed by requiring that each of at most T queries of the data be a simple summation of the result of applying a fixed function to the data pertaining to each privacy principal, and queries beyond the $T^{th}$ are not answered.

In addition to the above, so-called secure function evaluation techniques, developed in the 1980's, were a major advance in the ability of people, organizations, or other entities ("privacy principals") to compute a collective result without disclosing their individual data to one another. Secure function evaluation is explored in a variety of academic publications. For a background discussion of secure function evaluation, please refer to Ben-Or, Goldwasser, and Wigderson,"Completeness Theorems for Non-Cryptographic Fault-Tolerant Distributed Computation" (1988), and/or Goldreich, Micali, and Wigderson, "How to Play Any Mental Game" (1987).

SUMMARY

The present invention provides systems and methods for preserving privacy of data used in calculating an output. Privacy of data can be preserved while utility of the output is maximized by selecting from an appropriately calculated distribution of noise values to add to an output. A distribution that includes a high likelihood of large noise values may lead to less useful output data. Conversely, a distribution that includes very low likelihood of large noise values may lead to less privacy. A distribution should be calculated to provide an appropriate level of output utility and privacy based on the query that is performed and the desired privacy level. To tailor a distribution to a particular query, a particular query or dataset can be evaluated to determine the maximum difference in a collective output that can be produced by varying the data of an individual privacy principal. Such maximum difference is referred to herein as the "diameter" of the query. An appropriate distribution of noise values can then be calculated based on the diameter. A privacy-enhancing parameter, referred to herein as"epsilon," can be used when calculating a noise distribution to achieve any desired level of privacy. Other advantages and features of the invention are described below.

BRIEF DESCRIPTION OF THE DRAWINGS

The systems and methods for preserving privacy of data used in calculating an output in accordance with the present invention are further described with reference to the accompanying drawings in which.

DETAILED DESCRIPTION

Certain specific details are set forth in the following description and figures to provide a thorough understanding of various embodiments of the invention. Certain well-known details often associated with computing and software technology are not set forth in the following disclosure, however, to avoid unnecessarily obscuring the various embodiments of the invention. Further, those of ordinary skill in the relevant art will understand that they can practice other embodiments of the invention without one or more of the details described below. Finally, while various methods are described with reference to steps and sequences in the following disclosure, the description as such is for providing a clear implementation of embodiments of the invention, and the steps and sequences of steps should not be taken as required to practice this invention.

First, concepts associated with the query or dataset diameter will be introduced and examples to illustrate this concept will be set forth.

A query is a function applied to data. In a simple case, a query function may ask a database, for each person (privacy principal) in the database, does the person have blue eyes? If yes, the function returns a 1(one) and if no, it returns a 0(zero). A collective output may then be calculated by summing the individual outputs.

Extending the eye color example, imagine a database that contains eye color data for a plurality of people. Each person may have just one eye color, brown, blue, or green. A hypothetical attacker determined to find the true eye color of a particular person but that only has access to collective outputs from the database might see a collective output of a brown eye query and find that 82 people have brown eyes.

Next, two privacy principals, including the individual the attacker is interested in, leave the database. The attacker views the collective outputs of a subsequent query, finding that 81 people have brown eyes. Now the attacker knows there is some likely chance that the individual has brown eyes. If the attacker further knows that one of the departing privacy principals has blue eyes, he learns with certainty that the other has brown eyes.

When random noise is added to the collective outputs, the attacker's task becomes more difficult. However, noise also decreases the accuracy and therefore utility of the output. Noise is some undisclosed value that is added to an output, thereby generating a noisy output. Noise should ideally be sufficient to stymie the attacker but not so great that it overly impacts output utility.

The exact value of noise added to a particular collective output cannot be disclosed—if it were, there would be no point in adding noise. However, a distribution that describes the likelihood of possible noise values can be disclosed, so that all people viewing the collective outputs are aware of the likelihood that the noisy collective output is close to the actual collective output.

Figure 2A:
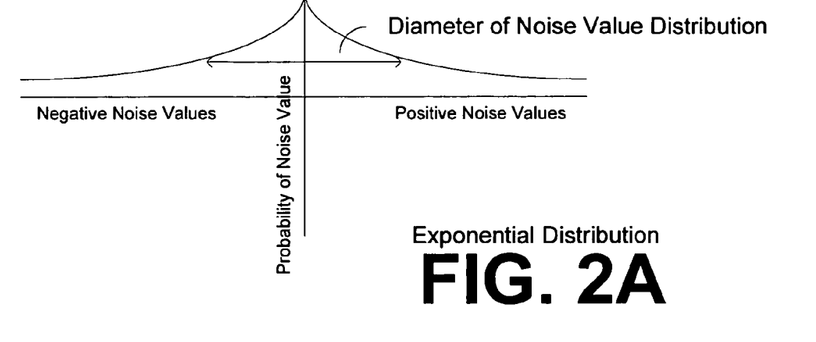
FIG. 2A illustrates an exponential distribution of possible noise values to add to a collective output.
Figure 2B:
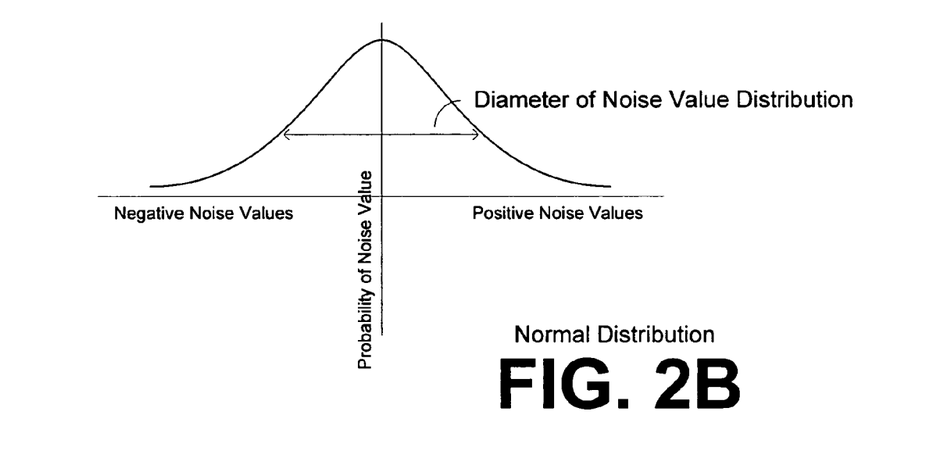
FIG. 2B illustrates a normal distribution of possible noise values to add to a collective output.
Figure 2C:
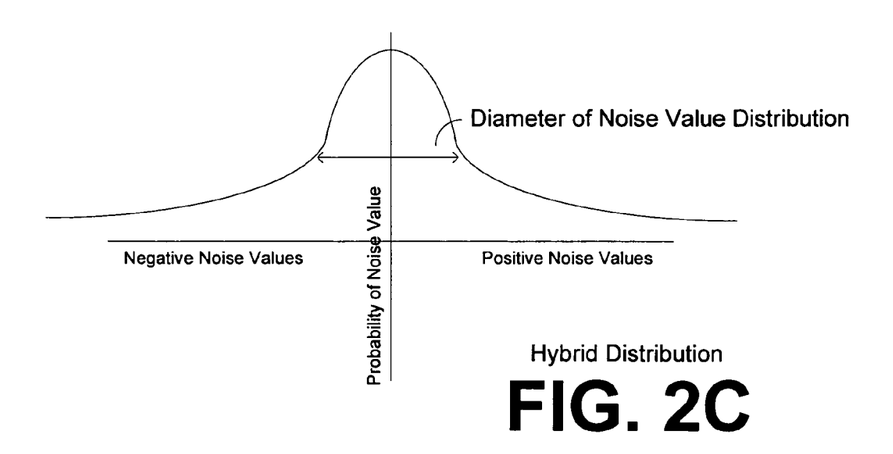
FIG. 2C illustrates a hybrid distribution of possible noise values to add to a collective output.

What noise distributions are appropriate? In the eye color example above, imagine a corresponding noise distribution makes it equally likely that a noise value anywhere from −100 (negative one hundred) and 100 (one hundred) is added. Noise values with an absolute value above 100are very unlikely. Such a distribution would surely protect privacy, but in this case at an unacceptably high utility cost. If the true number of people with brown eyes is 82 (eighty-two), but the noisy output is equally likely to be anywhere from −18 to 182, those wanting some realistic prediction of how many people have brown eyes will not be satisfied. Note that there are a number of other reasons this type of noise distribution is undesirable. For example, if all noise values in the range [−100,100] are equally likely, and noise value probability plummets down outside this range, the adversary would know upon seeing an output of −100(negative one hundred) that the original value was 0(zero), and not 1 (one). Distributions such as those of FIG. 2A-2C are preferable because they have the property that 0(zero) is the most likely, while the likelihood of other noise values decreases with their distance from 0(zero).

Conversely, if the noise distribution makes it equally likely that a noise value between −0.001 (negative one one thousandth) and 0.001 (one one thousandth) will be added to the collective result, but very unlikely that noise with an absolute value beyond 0.001 will be added, then the noise distribution will lead to very high output utility, but at the expense of privacy. In this case, the privacy principals will have no meaningful additional privacy due to noise, because the attacker can simply round to the nearest whole number. If the disclosed noisy output is 81.999 people with brown eyes, the attacker knows that the actual collective output was probably 82.

To determine an appropriate noise distribution, we propose evaluating a query to determine the maximum difference in the collective output attributable to a particular privacy principal. We refer to this maximum difference as the diameter of a query. In the brown eye query example above, the diameter is 1 (one). Either a principal has brown eyes, in which case she increases the output of a brown eye query by 1 (one), or she does not have brown eyes, in which case she does not increase the collective output of a brown eye query at all.

Thus, an exemplary appropriate noise distribution can comprise a high likelihood that a noise value of −1 (negative one),0 (zero), or 1 (one) will be added to the collective result, a somewhat lower likelihood of a noise value with an absolute value of 2 (two), still less likelihood of noise with an absolute value of 3 (three), and so forth. The diameter of a query can thus be used to determine an appropriate distribution of noise values.

Now consider a slightly different database that also contains eye color data for a plurality of people. This time, however, the database accounts for the fact that some people have a first eye with a first color, and a second eye with a second color. Therefore, the database allows a person to have a maximum of two eye colors, e.g. brown and blue, brown and green, or blue and green.

A query can ask,"How many people have at least one brown eye and how many people have at least one blue eye?" The diameter of such a query is 2 (two). That is, any one principal can make a maximum difference of 2 (two) to the collective output. Such a principal may have one brown eye and one blue eye in which case she causes each of a brown eye output and a blue eye output to increase by 1 (one). Alternatively, if the principal leaves the database, the effect will be that her data adds nothing (zero) to each of the outputs. Therefore the diameter of the query is 2 (two).

It should be noted that the diameter concept can be applied to datasets as well as queries. For example, the dataset associated with the U.S. Census might be analyzed, a diameter could be calculated for the entire dataset, and the diameter measurement could subsequently apply to any queries that are performed over the dataset. Dataset analysis to choose a diameter may be imperfect in some situations, resulting in diameter measurements that are too large or too small for a particular query. Dataset diameter measurements may nonetheless be an improvement in that the dataset diameter helps tailor the noise distribution to some degree. Such embodiments may be appropriate in situations where query analysis is difficult or computationally expensive.

The problem of computing the diameter is not always easily solved. In one embodiment, diameter is determined by analyzing a query function. For example, interested persons may analyze functions of interest, and publish papers proving bounds on their diameters. These functions with proven bounds will be used in conjunction with various implementations the invention. For various sets of related simple query functions, algorithms for analyzing the function and computing a diameter for an arbitrary function f within the set may also be developed.

In other embodiments, diameter of a function may be determined empirically. Empirical diameter determinations are risky because they may result in inappropriately scaled noise distributions. Nonetheless, empirical diameter determinations may be appropriate in certain settings. Empirical diameter determinations may be made, for example, by varying actual data in a database, running queries, and measuring differences in resulting collective outputs. Analytical diameter determinations are considered preferable, however, because they allow for quantifying diameter over all possible databases, not just a single database.

While the diameter of a query can be used to determine an appropriate distribution of noise values; diameter need not be the only variable in shaping a distribution. Another variable, referred to herein as epsilon, is a privacy parameter that may be used to increase or decrease the amount of privacy that is ensured. When epsilon is used to widen the distribution of possible noise values, it enhances privacy beyond the amount that would be ensured by using diameter alone in a particular distribution equation. Conversely, if epsilon is used to narrow the distribution, it decreases privacy from what would be obtained using diameter alone. Thus, epsilon values can represent an amount of enhanced privacy. The extent to which epsilon impacts privacy can be tailored by the distribution equation that is selected.

Preferred embodiments will therefore utilize a privacy parameter, as well as a diameter measurement, to generate a noise distribution. Embodiments that do not use a privacy parameter will effectively set epsilon to 1 (one) which corresponds to some amount of privacy loss that may be more or less than desired in the particular situation.

The concepts introduced above will now be revisited and exemplary calculations that may be used in systems and methods incorporating the query diameter concept will be set forth.

For any arbitrary query functions, the magnitude of noise values that are likely to be added to the collective outputs can be tailored to the query functions. We first view a collection of query functions as a single function, hereafter "f", which has multiple outputs. For each privacy principal "p" we can measure the diameter "diam" of their possible values under f: the maximum difference in f that can be attained by varying the data of the principal while holding the rest of the data constant.

$$\text{diam}(f,p) = \max\_\{x,y: x, y \text{ disagree only on } p\} \|f(x)-f(y)\|$$

Here we are measuring distance by looking at the size of $\|f(x)-f(y)\|$, and there are several possible ways to measure this quantity. We will describe two, and the different noise distributions they suggest.

$$\text{diam1}(f, p) = \max\_\{x,y: x, y \text{ disagree only on } p\} \|f(x)-f(y)\|\_1$$

$$\text{diam2}(f, p) = \max\_\{x,y: x, y \text{ disagree only on } p\} \|f(x)-f(y)\|\_2{}^2$$

Knowing the diameter of a function f with respect to a principal p, we can ensure a certain degree of privacy simply by choosing to add appropriately distributed noise to the answer f(x) before returning it. Two examples of noise distributions include:

noise~exp(-\epsilon$\|x\|$/diam1(f,p))//"exponential"
noise—see FIG. 2A.

noise~exp(-\epsilon$\|x\|^2$/diam2(f,p))//"normal"
noise—see FIG. 2B.

Here \epsilon is a privacy parameter that determines an amount of privacy that is ensured. Note that in this embodiment, an epsilon of zero will correspond to zero privacy loss, but will also render the database useless because the amount of added noise becomes infinite.

The concepts introduced above will now be revisited once again, and elaborated with reference to appended FIG. 1-FIG. 4.

Figure 1:
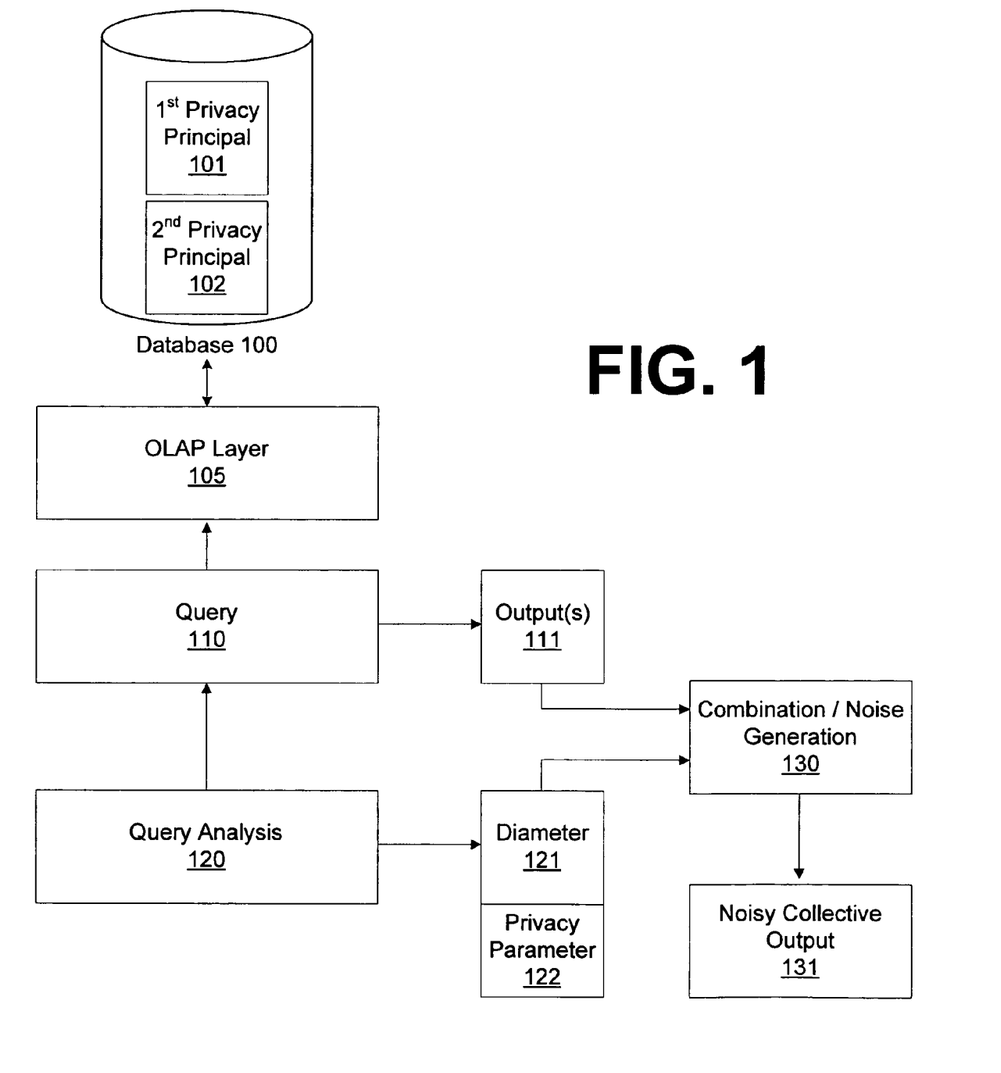
FIG. 1 illustrates a system for generating a noisy collective output 131, wherein said system preserves privacy of data used in calculating said noisy collective output

FIG. 1 presents a system for generating a noisy collective output 131, wherein said system preserves privacy of data used in calculating said noisy collective output 131. A database 100 is configured to store data associated with a plurality of privacy principals 101, 102 and configured with a query mechanism 110 to run queries on said data to obtain a plurality of outputs 111. The database 100 may be configured with an Online Analytical Processing (OLAP) Layer 105. Outputs 111 can be combined to produce a collective output. In FIG. 1, output 111 combination could occur, for example, in a noise generation mechanism 130 that both combines outputs 111 and calculates an amount of noise to add to the combined outputs, then reveals a noisy collective output 131.

A database 100 is a collection of data, typically describing the activities of one or more related organizations, people, or other entities referred to herein as privacy principals. For example, a university database might contain information about entities, such as students, faculty, courses, and classrooms, and relationships between entities, such as student enrollment in courses, faculty teaching courses, and the use of rooms for courses. A database management system, or DBMS, is software designed to assist in maintaining and utilizing large collections of data. For the purpose of this document, however, the term"database," or"database server" refers to either or both of a collection of data and DBMS software. Thus, database 100 illustrates a database server comprising both collections of data and DBMS. Note that as such database 100 may include the various other elements presented in FIG. 1 which are illustrated separately to clearly suggest the operation of the invention.

Various DBMS products, e.g. MICROSOFT SQL SERVER®, IBM DB2®, ORACLE DATABASE®, and SYBASE IQ® have greatly extended the capabilities of databases. Databases can store a wide variety of data types, such as images and text, and can perform complex queries on stored data. Specialized systems have been developed by numerous vendors for creating data warehouses, consolidating data from several databases, and for carrying out specialized analysis. All such products and database configurations are suitable for use in connection with the systems and methods herein.

Query mechanism 110 can perform any desired queries over data in databases. Queries can be simple or complex, and can generate single outputs or multiple outputs. Also, a privacy principal can be any defined entity or group of entities.

A query analysis mechanism 120 determines a maximum difference in a collective output, or diameter 121 of a particular query. A query need not actually be run against the data in database 100 in order to analyze the query. Query analysis can proceed by analysis of the query itself, thereby determining the query diameter 121. Query analysis can be implemented in a plurality of acceptable ways.

In one embodiment, query analysis proceeds by finding a predetermined query diameter. For example, interested persons may analyze functions of interest, and publish papers proving bounds on their diameters. These functions with proven bounds will be used in conjunction with various implementations the invention. Query analysis mechanism 120 may thus match a query to a known diameter for said query.

In another embodiment, query analysis may recognize a query as from a set of related simple query functions for which query analysis algorithms are available. An appropriate algorithm may be applied to analyze the function and compute a diameter.

In other embodiments, diameter of a function may be determined empirically. As mentioned above, empirical diameter determinations are risky because they may result in inappropriately scaled noise distributions. Nonetheless, empirical diameter determinations may be appropriate in certain settings.

For example, in one embodiment, query analysis might actually take up a privacy principal 101 in database 100, save the initial state of the privacy principal 101, and then run a query against it a number of times, varying the data by altering it each time, to determine the query diameter. After testing to determine a diameter in this fashion, the privacy principal may be returned to its original state. In this embodiment, an actual collective output need not be calculated to determine query diameter. Instead it is simply known that outputs 111 can be combined to produce a collective output, and that if they are, the diameter in said collective output from varying data associated with a privacy principal 101 can be used to generate an appropriate noise distribution for such a collective output.

In another embodiment, the query itself can be analyzed without the need to actually run the query or alter the data of a privacy principal 101. Instead, the diameter is determined by varying the data of a hypothetical first privacy principal. In effect, a hypothetical first privacy principal is constructed that would have a maximum impact on a collective result. While no actual data in a privacy principal is altered, this is described herein as varying the data of a first privacy principal, because the data of such hypothetical principal is "varied" to the point at which it will have maximum impact. Meanwhile, the data associated with one or more hypothetical second privacy principals is effectively held constant by the assumption that such data does not change when measuring diameter using the hypothetical first principal.

It should be noted that it is preferable to make diameter determinations with regard for all possible databases, not just one single actual database. The analytic approach for determining diameter can account for all databases. The empirical approach may require The system of FIG. 1 further comprises a noise generation mechanism 130. This mechanism may include a variety of functions, which may be outsourced to individual components or conducted by 130 as shown. Noise generation mechanism 130 calculates, using said diameter 121, a distribution of possible noise values to add to a collective output. The equations illustrated above provide exemplary approaches to calculating noise distributions. Exemplary noise distributions are further illustrated in FIG. 2A-2C.

FIG. 2A-2C depict noise values along an x-axis, and probabilities associated with such noise values on the y-axis. Thus, a noise value on the x-axis corresponding to a high value on the y-axis has a high probability of being selected. The illustrated distributions all share a beneficial feature of decreasing the probability a given noise value as its absolute value increases. This allows noisy outputs to nonetheless be useful, because the probability of an excessively high noise value can be remote.

FIG. 2A illustrates an exponential distribution, as will be recognized by those of skill in mathematics. FIG. 2B illustrates a normal distribution. FIG. 2C represents a hybrid distribution. The hybrid distribution of FIG. 2C is a normal and exponential distribution, such that a normal distribution defines a portion of the distribution comprising the most probable noise values, i.e. those with a higher y-axis value, and an exponential distribution defines a portion of the distribution comprising the least probable noise values, i.e. those with low y-axis values, corresponding to larger absolute values on the x-axis.

A diameter measurement can be used in calculating each of the distributions in FIG. 2A-2C. A large diameter value will widen the distribution, increasing the probability that larger x-axis (noise) values will be used. Conversely, a small diameter will decrease the likelihood of large noise values. The exemplary equations provided above are satisfactory, and those of skill in the art will be able to construct an infinite variety of distributions that successfully utilize a diameter measurement to create a satisfactory noise distribution. For example, an infinite number of small modifications to the distributions depicted in FIG. 2A-2C are possible.

The mechanism for calculating a noise distribution 130 may be configured to modify a noise distribution using a privacy parameter 122, wherein said privacy parameter 122 corresponds to an amount of privacy that is ensured. We refer to the privacy parameter as epsilon. An epsilon that effectively widens the distributions illustrated in FIG. 2A-2C will provide enhanced security and vice-versa. In the equations set forth above, epsilon is contemplated to be a less than one number in a denominator, with diameter in the numerator. Thus, a small epsilon leads to higher privacy. Any numbers of other ways to implement a privacy parameter are available to the skilled mathematician.

A system such as that illustrated in FIG. 1 can be used to protect the privacy of any types of data. For example, the data may be medical information, and the privacy principals may be people. The data may also comprise information submitted to a government agency, such as the Internal Revenue Service (IRS), wherein the privacy principals could be private individuals, companies, and /or other organizations.

To further demonstrate the usefulness of this approach to noise distribution, a few examples of applications that were not possible in the previous frameworks may be instructive. Adding noise to collective outputs in the two examples below was not previously possible either because the queries could not be represented as summations, or because adding noise that depends only on a number of queries rendered the data useless.

First, so-called k-Means is a popular data analysis algorithm, that operates by iteratively asking a collection of data points for their averages under various partitions. Importantly, each point participates in at most one of the parts at a time, and as a consequence the number of parts does not enter into the amount of noise added. A system such as FIG. 1 can significantly improve the quality of the results given back, as the magnitude of noise is so much smaller.

Second, there are many situations where a firm may be interested in determining if they have the resources (staff, equipment, etc) to carry out a certain number of contracts, or more generally to determine the largest number of contracts they could fulfill with their current resources. In many cases it is important that their decision not leak information about their resources, either from the point of view of competitive advantage, or owing to privacy legislation. In either case, resource allocation commonly has the low diameter property: the presence or absence of a single employee is unlikely to change the total number of satisfiable contracts by more than a small amount. A single person can only do so much, and their absence only precludes those few things that they would otherwise have done. As such, this function can be computed and released noisily, ensuring the confidentiality of the particular resources that the firm has, while disclosing their capability of fulfilling the contracts. Importantly, it is unclear how this question could have been expressed in terms of a summation, and the more flexible diameter based perturbation allows computation that would not have been possible before.

Figure 3:
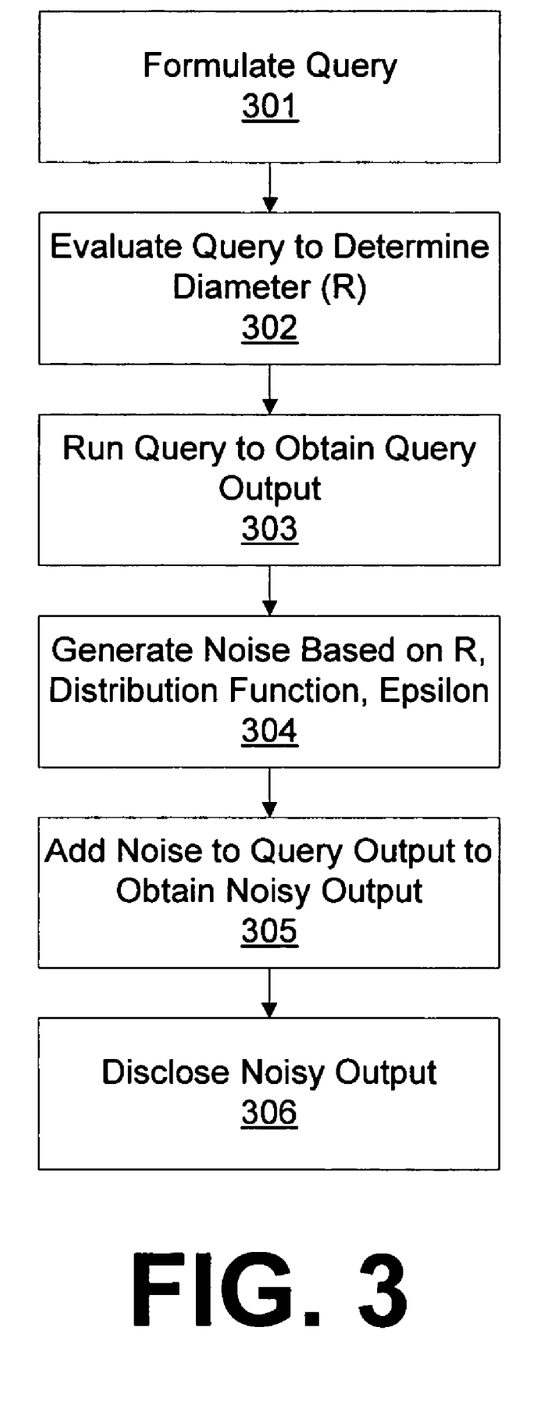
FIG. 3 illustrates a method for preserving privacy of data used in calculating an output.

With reference to FIG. 3, a method for preserving privacy of data used in calculating an output is illustrated. The method comprises first formulating whatever query is to be run against data in a database 301. Next, the query can be evaluated to determine a diameter (represented by the letter R) 302. The query can be performed on data associated with a plurality of privacy principals to obtain a plurality of outputs, and said plurality of outputs can be combined to produce a collective output. Evaluating the query 302 to determine a diameter comprises determining a maximum difference in said collective output from varying data associated with a first privacy principal while holding constant data associated with one or more second privacy principals, as explained above.

The query can be run in step 303, or this step may be postponed until after calculating an appropriate noise distribution in step 304. Calculating an appropriate noise distribution 304 comprises calculating using said diameter (maximum difference) a distribution of possible noise values to add to said collective output. The calculation may also make use of a privacy parameter that corresponds to an amount of privacy that is ensured. The calculation may contemplate any type of distribution curves, for example the exponential distribution in FIG. 2A, the normal distribution in FIG. 2B, or a hybrid distribution such as that of FIG. 2C.

Once a query is performed on said data associated with a plurality of privacy principals, the collective output from the query can be calculated, and a noise value from the calculated distribution can be added to the collective output to produce a noisy collective output 305. Finally, the collective noisy output can be disclosed 306, as can the noise distribution.

One interesting aspect of the invention is that it permits a useful backwards operation in which, for a give query diameter and a know noise distribution, the value of the privacy parameter epsilon can be determined. Thus, systems using the invention that disclose a query and a noise distribution also verifiably disclose the value of the privacy parameter that was used. Privacy principals can thus be informed or calculate for themselves the degree of privacy that is being used with their data.

Figure 4:
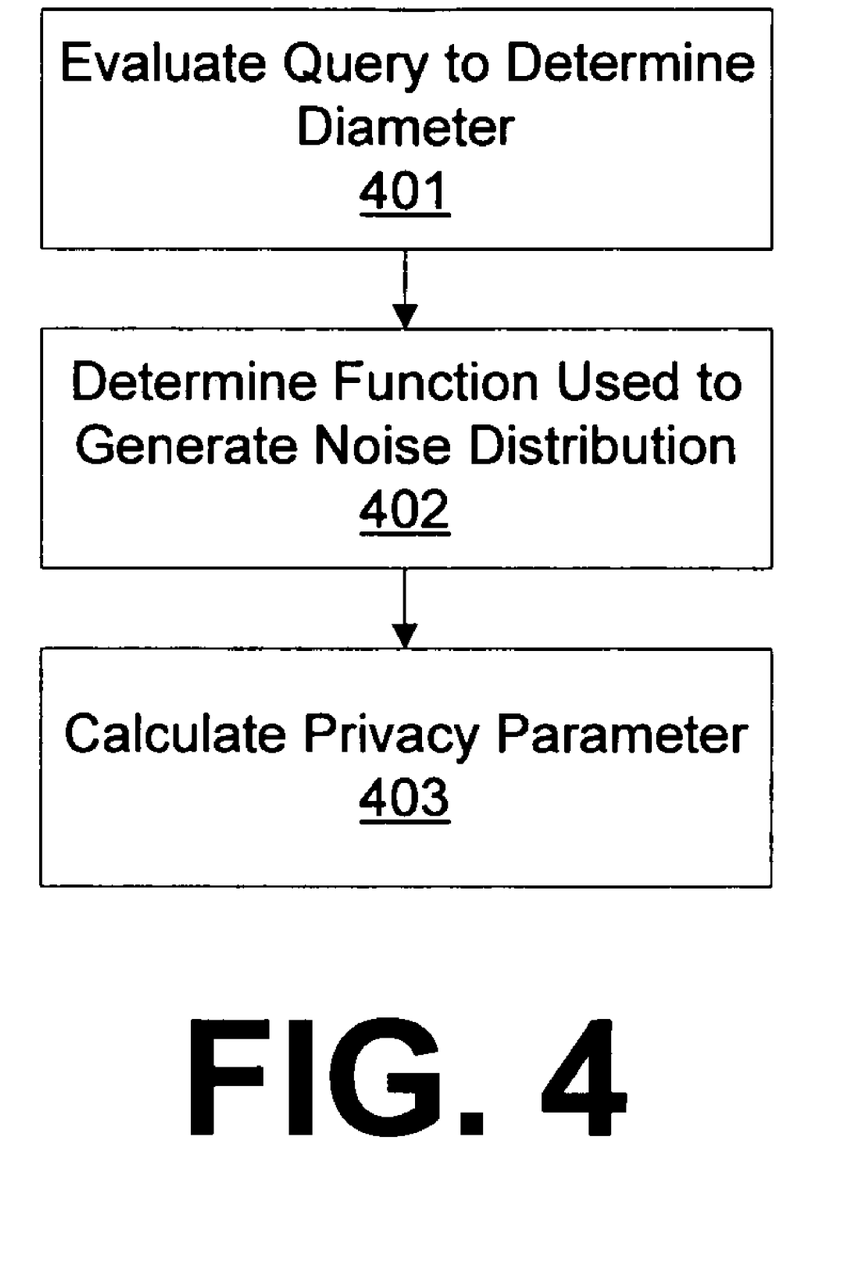
FIG. 4 illustrates a method for determining an amount of privacy guaranteed to privacy principals supplying data, wherein said data is used in calculating a collective noisy output.

A privacy principal that wished to calculate the privacy parameter that is being used with her data might carry out a method such as that illustrated in FIG. 4. Such a method is for determining an amount of privacy guaranteed to privacy principals supplying data, wherein said data is used in calculating a collective noisy output. The method comprises determining a query diameter 401, that is, determining a maximum difference in a collective output from varying data associated with a first privacy principal while holding constant data associated with one or more second privacy principals. Next, determine the distribution function that was used to generate a noise distribution 402. In the examples provided herein the distribution function has two variables: diameter (also referred to as maximum difference of a collective output) and epsilon, i.e. a privacy parameter corresponding to an amount of guaranteed privacy. If the distribution function and the diameter are known, epsilon can be calculated 403.

The various systems and methods discussed herein are contemplated to be carried out by one or more computing devices which are, in general, well understood. A computing device typically includes at least some form of computer readable media. Computer readable media can be any available media that can be accessed by the device. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can accessed by a device. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

In addition to the specific implementations explicitly set forth herein, other aspects and implementations will be apparent to those skilled in the art from consideration of the specification disclosed herein. It is intended that the specification and illustrated implementations be considered as examples only, with a true scope and spirit of the following claims.

The invention claimed is:

1. A method for preserving privacy of data used in calculating an output, said method comprising:
    performing a query over data, thereby obtaining an output;
    calculating a noise distribution at least in part using a diameter of said query, wherein said diameter defines a maximum difference in said output attributable to a privacy principal associated with said data;
    selecting a noise value from the noise distribution;
    combining said noise value with the output, thereby obtaining a noisy output that preserves privacy of said data,
    wherein said noise distribution is a hybrid normal and exponential distribution, such that a normal distribution defines a portion of the distribution comprising the most probable noise values, and an exponential distribution defines a portion of the distribution comprising the least probable noise values.

2. The method of claim 1, wherein said data is in a database.

3. The method of claim 2, wherein said data in a database is associated with at least one privacy principal.

4. The method of claim 1, wherein said calculating a noise distribution further comprises at least in part using a privacy parameter, wherein said privacy parameter corresponds to an amount of privacy that is ensured.

5. The method of claim 1, wherein the data comprises medical information.

6. The method of claim 1, wherein the data comprises information submitted to a government agency.

7. The method of claim 1, wherein the data comprises information about company resources.

8. A system for generating a noisy output, wherein said system preserves privacy of data used in calculating said noisy output, said system comprising:
- a processor;
- a memory;
- a database, said database configured to store data associated with a plurality of privacy principals and configured to run queries on said data to obtain an output; and
- a noise generation mechanism that at least in part utilizes a diameter of a query to produce a noise distribution, wherein said diameter defines a maximum difference in said output attributable to a privacy principal, and wherein a noise value is selected from said noise distribution and combined with the output,
- wherein said noise distribution is a hybrid normal and exponential distribution, such that a normal distribution defines a portion of the distribution comprising the most probable noise values, and an exponential distribution defines a portion of the distribution comprising the least probable noise values.

9. The system of claim 8, further comprising query analysis mechanism for determining query diameter.

10. The system of claim 9, wherein said query analysis mechanism is configured to retrieve predetermined query diameters.

11. The system of claim 8, wherein said noise generation mechanism is configured to modify said noise distribution using a privacy parameter, wherein said privacy parameter corresponds to an amount of privacy that is ensured.

12. The system of claim 8, wherein the data comprises medical information.

13. The system of claim 8, wherein the data comprises information submitted to a government agency.

* * * * *

UNITED STATES PATENT AND TRADEMARK OFFICE
CERTIFICATE OF CORRECTION

PATENT NO.        : 7,769,707 B2                               Page 1 of 1
APPLICATION NO.   : 11/291131
DATED             : August 3, 2010
INVENTOR(S)       : Cynthia Dwork et al.

It is certified that error appears in the above-identified patent and that said Letters Patent is hereby corrected as shown below:

In column 1, line 51, delete "11/298,563,and" and insert -- 11/298,563, and --, therefor.

In column 1, line 57, delete "Sheffy" and insert -- Sherry --, therefor.

In column 1, line 59, delete "Sheffy" and insert -- Sherry --, therefor.

Signed and Sealed this
Fifteenth Day of February, 2011

David J. Kappos
*Director of the United States Patent and Trademark Office*